(12) United States Patent
Chang et al.

(10) Patent No.: US 9,810,645 B2
(45) Date of Patent: Nov. 7, 2017

(54) SYSTEM AND METHOD FOR MEASURING PERMITTIVITY

(71) Applicant: National Tsing Hua University, Hsinchu (TW)

(72) Inventors: Tsun-Hsu Chang, Hsinchu (TW); Hsein-Wen Chao, Hsinchu (TW); Wei-Syuan Wong, Hsinchu (TW)

(73) Assignee: NATIONAL TSING HUA UNIVERSITY, Hsinchu (TW)

( * ) Notice: Subject to any disclaimer, the term of this patent is extended or adjusted under 35 U.S.C. 154(b) by 107 days.

(21) Appl. No.: 14/664,228

(22) Filed: Mar. 20, 2015

(65) Prior Publication Data

US 2016/0146742 A1 May 26, 2016

(30) Foreign Application Priority Data

Nov. 26, 2014 (TW) .............................. 103141048 A

(51) Int. Cl.
*G01R 27/04* (2006.01)
*G01N 22/00* (2006.01)
*G01N 27/04* (2006.01)

(52) U.S. Cl.
CPC ............. *G01N 22/00* (2013.01); *G01N 27/04* (2013.01)

(58) Field of Classification Search
CPC .............................. G01N 22/00; G01N 27/221
See application file for complete search history.

(56) References Cited

U.S. PATENT DOCUMENTS 5,119,034 A * 6/1992 Ishikawa ............ G01R 27/2658
219/690
2002/0101307 A1* 8/2002 Liu .......................... H01P 7/06
333/230

OTHER PUBLICATIONS

Li et al., Design of a Cylindrical Cavity Resonator for Measurements of Electrical Properties of Dielectric Materials, 2010.*

* cited by examiner

*Primary Examiner* — Daniel Miller
(74) *Attorney, Agent, or Firm* — Muncy, Geissler, Olds & Lowe, P.C.

(57) ABSTRACT

A system for measuring a permittivity includes a resonant chamber, a conductive probe, a platform, a pillar, a detector, and a computing module. The resonant chamber has a cavity. The conductive probe is configured for introducing a microwave into the cavity of the resonant chamber. The platform is configured for carrying a sample. The pillar is positioned between the platform and a chamber wall, so that the platform protrudes from the chamber wall. The detector is used to detect a resonant frequency of the microwave when resonance occurs within the cavity. The computing module is configured for calculating a permittivity corresponding to the measured resonant frequency according to a corresponding relationship between resonant frequency and permittivity. The above-mentioned system for measuring a permittivity is capable of measuring a broader range of permittivity with simplified measurement steps and higher accuracy. A method for measuring a permittivity is also disclosed.

17 Claims, 4 Drawing Sheets

SYSTEM AND METHOD FOR MEASURING PERMITTIVITY

BACKGROUND OF THE INVENTION

1. Field of the Invention

The present invention relates to a measuring system and method, and particularly to a system and method for measuring a permittivity.

2. Description of the Prior Art

As to a conventional method for measuring a permittivity, a sample is disposed within a resonant chamber, and a microwave is introduced into the resonant chamber to measure a resonant frequency when resonance is generated. The resonant frequency is used to calculate a permittivity of the sample. As to the conventional measuring method, before measuring a sample, there is needed that a system calibration is performed with a sample having a known permittivity. That is, a sample having a known permittivity is disposed within the resonant chamber, and a resonant frequency is measured to calculate the system parameters. However, the conventional measuring method has more complex steps, and measurement error of a permittivity also increases for those away from the calibration point. Therefore, the measurement of the conventional method has a relatively narrower range. In addition, the conventional method for measuring a permittivity only causes smaller perturbations of the resonance system. In other words, small perturbations generated by unexpected factors will impact the accuracy of the measured permittivity.

To sum up the foregoing descriptions, how to measure a permittivity simply and accurately is the current target.

SUMMARY OF THE INVENTION

The present invention provides a system and method for measuring a permittivity, which enhances the electric field intensity around a sample, such that a signal of a resonant system is amplified by the sample. Since small perturbations generated by unexpected factors have less impact on the accuracy of the measured permittivity, the system and method for measuring a permittivity of the present invention therefore may greatly enhance the accuracy of the measurement.

A system for measuring a permittivity of one embodiment of the present invention comprises a resonant chamber, a conductive probe, a platform, a pillar, a detector, and a computing module. The resonant chamber has a cavity. The conductive probe passes through a chamber wall of the resonant chamber and is configured to introduce a microwave into the cavity of the resonant chamber. The platform is disposed in the cavity of the resonant chamber and is configured to carry a sample. The pillar is disposed between the platform and the chamber wall so that the platform protrudes from the chamber wall to enhance an electric field intensity around the sample so as to amplify a perturbation of the resonant chamber by the sample. The detector is configured to detect the resonant frequency of the microwave when resonance occurs within the cavity. The computing module is configured to calculate a permittivity corresponding to the resonant frequency of the sample within the cavity measured by the detector based on a corresponding relationship between resonant frequency and permittivity obtained from a simulation performed by an electromagnetic field simulation software.

A method for measuring a permittivity of another embodiment of the present invention comprises: providing a resonant chamber having a cavity and a platform, wherein the platform protrudes from a chamber wall of the resonant chamber with a pillar to enhance an electric field intensity around the sample so as to amplify a perturbation of the resonant chamber by the sample; disposing a sample on the platform; introducing a microwave into the cavity of the resonant chamber; detecting the resonant frequency of the microwave when resonance occurs within the cavity; and calculating a permittivity corresponding to the resonant frequency of the sample within the cavity based on a corresponding relationship between resonant frequency and permittivity obtained from a simulation performed by an electromagnetic field simulation software.

The objective, technologies, features and advantages of the present invention will become apparent from the following description in conjunction with the accompanying drawings wherein certain embodiments of the present invention are set forth by way of illustration and example.

BRIEF DESCRIPTION OF THE DRAWINGS

The foregoing conceptions and their accompanying advantages of this invention will become more readily appreciated after being better understood by referring to the following detailed description, in conjunction with the accompanying drawings, wherein.

DESCRIPTION OF THE PREFERRED EMBODIMENT

Figure 1:
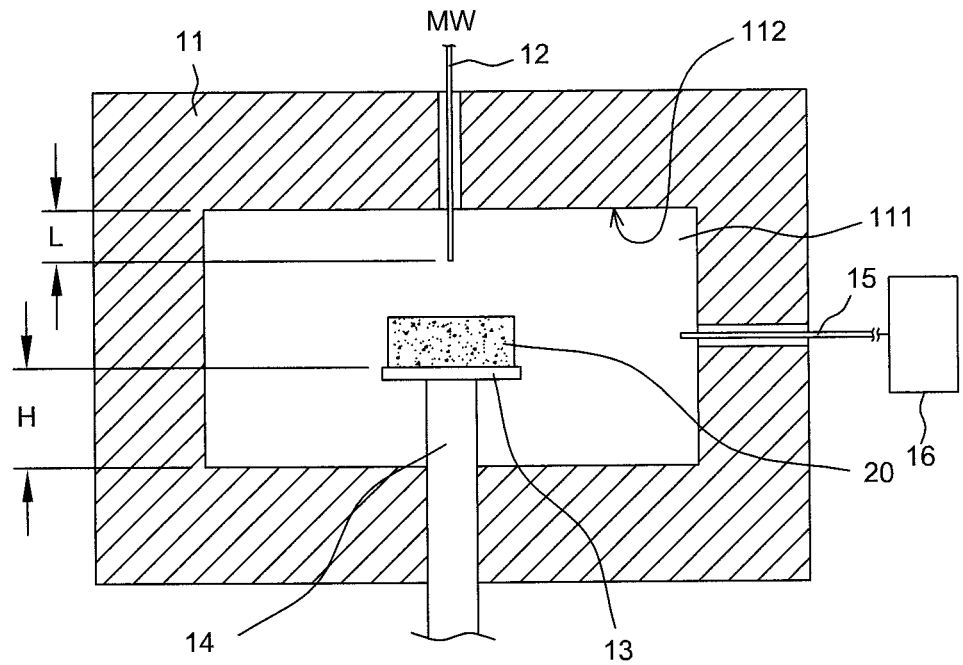
FIG. 1 is a schematic view, showing a system for measuring a permittivity of one embodiment of the present invention.
Figure 2:
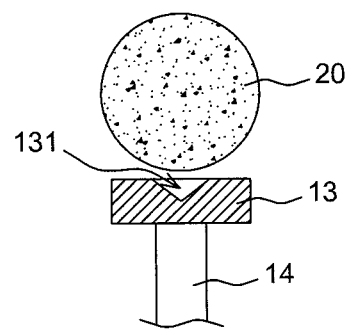
FIG. 2 is a schematic view, showing a platform of a system for measuring a permittivity of another embodiment of the present invention.

Referring to FIG. 1, a system for measuring a permittivity of one embodiment of the present invention comprises a resonant chamber 11, a conductive probe 12, a platform 13, a pillar 14, a detector 15, and a computing module 16. The resonant chamber 11 has a cavity 111. In one embodiment, the cavity 111 may be cylindrical. The conductive probe 12 passes through a chamber wall 112 of the resonant chamber 11 and protrudes from the chamber wall 112. The conductive probe 12 is configured to introduce a microwave MW into the cavity 111 of the resonant chamber 11. The platform 13 is disposed within the cavity 111 of the resonant chamber 11 and is used to carry a sample 20. In one embodiment, a carrying surface of the platform 13 may be a plane as shown in FIG. 1, or the carrying surface of the platform 13 may comprise a trench or notch 131 as shown in FIG. 2, so as to carry a sample 20 that is spherical or rolls easily. For example, the notch 131 may be conical or cylindrical. The pillar 14 is disposed between the platform 13 and the chamber wall 112 of the resonant chamber 11, so that the platform 13 protrudes from the chamber wall 112 of the resonant chamber 11. In one embodiment, the platform 13 and the pillar 14 may be cylindrical, and a diameter of the pillar 14 may be less than, equal to, or more than a diameter of the platform 13.

Figure 5:
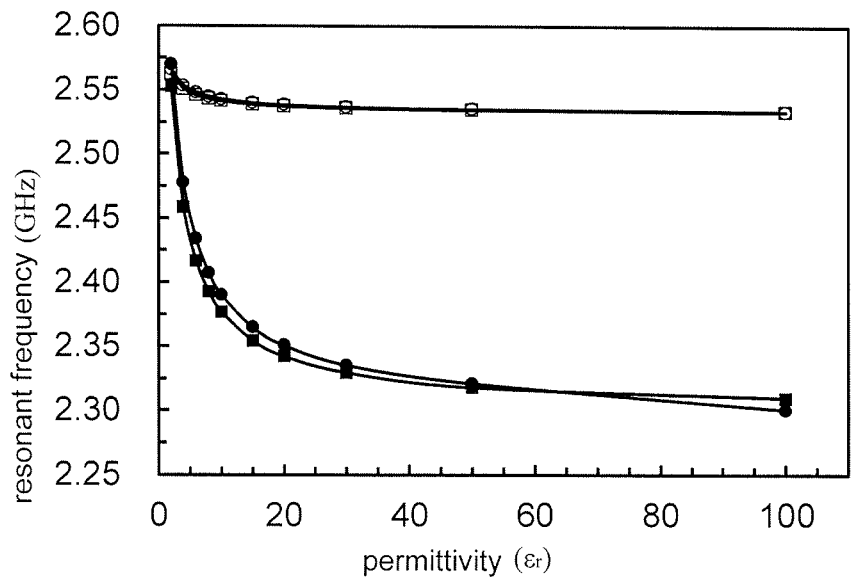
FIG. 5 is a curve diagram, showing a corresponding relationship between resonant frequency and permittivity.

Continued with the foregoing descriptions, the detector 15 is used to detect a resonant frequency of the microwave MW when resonance occurs within the cavity 111. The computing module 16, e.g., a computer or other similar devices having computing capability, compares the resonant frequency detected by the detector 15 with a corresponding relationship between resonant frequency and permittivity, so as to calculate a corresponding permittivity, i.e., the permittivity of the sample 20. In one embodiment, the corresponding relationship between resonant frequency and permittivity is obtained from a simulation performed by an electromagnetic field simulation software. For example, the simulation software may be a 3D electromagnetic field simulation software "High Frequency Structural Simulator (HFSS)" developed by the Ansoft Inc., which is incorporated by the ANSYS Inc. in 2008. The corresponding relationship between resonant frequency and permittivity may be presented in a comparison table or a curve diagram as shown in FIG. 5, so that the computing module 16 may calculate a permittivity corresponding to the measured resonant frequency according to the corresponding relationship.

Figure 3:
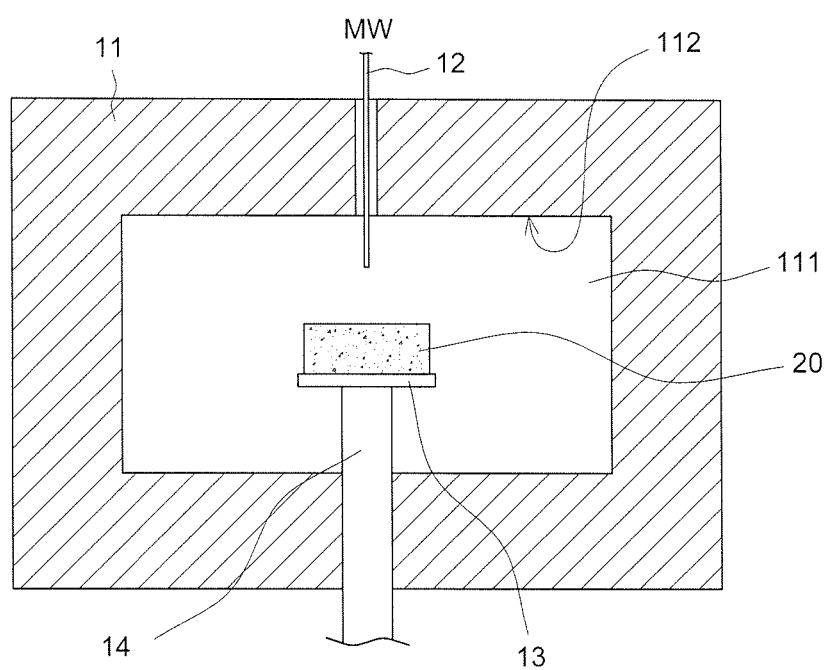
FIG. 3 is a schematic view, showing a system for measuring a permittivity of yet another embodiment of the present invention.

In the embodiment shown in FIG. 1, the conductive probe 12 and the platform 13 are disposed correspondingly to each other, but are not thus limited. A disposed position of the conductive probe 12 may be exchanged with that of the detector 15, i.e., an extending direction of the conductive probe 12 and an extending direction of the pillar 14 are perpendicular to each other. It can be understood that a non-perpendicular included angle may exist between the extending direction of the conductive probe 12 and the extending direction of the pillar 14. In one embodiment, the conductive probe 12 and the detector 15 may be integrated, as shown in FIG. 3.

In one embodiment, a length L of the conductive probe 12, which protrudes from the chamber wall 112, is adjustable. The protruding length L of the conductive probe 12 may be varied so as to adjust the amplitude of the resonance. In one embodiment, a height H of the platform 13, which protrudes from the chamber wall 112, is adjustable. The protruding height H of the platform 13 may be varied so as to adjust the resonant frequency of the system.

According to the above-mentioned configuration, the system for measuring a permittivity of the present invention does not need to calibrate the measuring system with a sample having a known permittivity. Thus, measuring steps of the present invention are simpler and more convenient. Moreover, the pillar 14 protrudes the platform 13 from the chamber wall 112 of the resonant chamber 11 so as to enhance the electric field intensity around the sample 20. Therefore, compared to conventional measuring methods, a signal of the resonant system is amplified the sample. In other words, small perturbations generated by unexpected factors cause less influences on the accuracy of the measured permittivity. Therefore, the system and method for measuring a permittivity of the present invention may greatly enhance the accuracy of the measurement.

Figure 4:
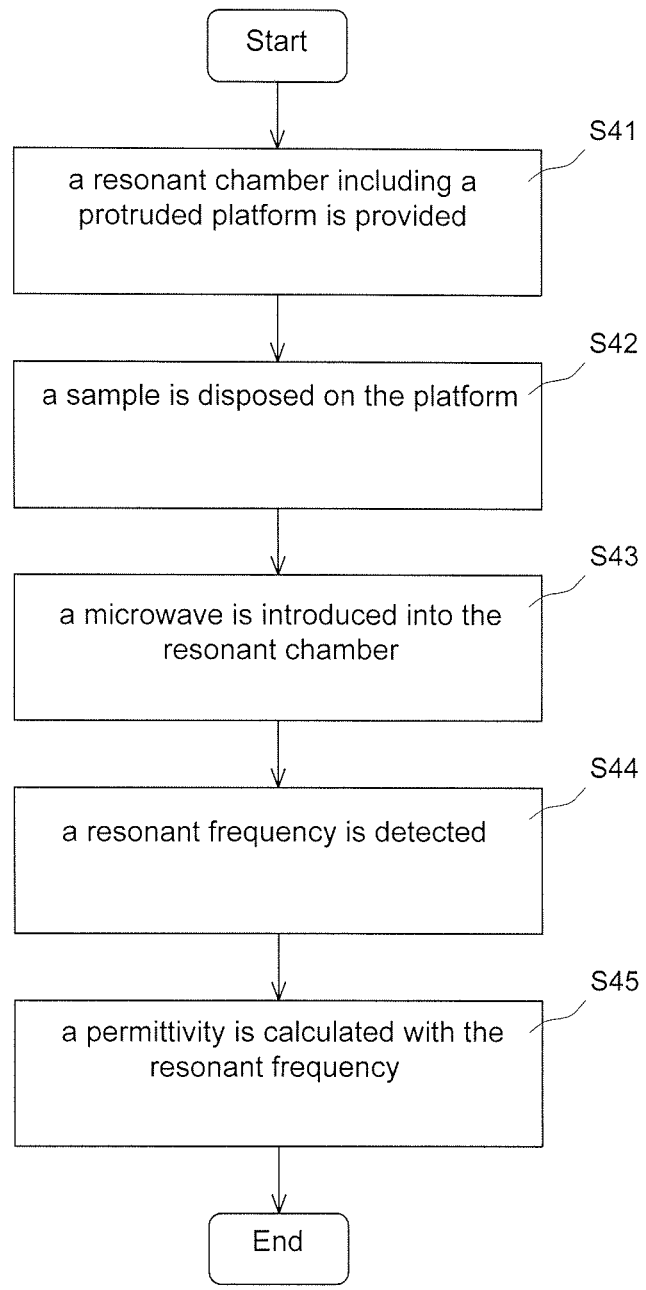
FIG. 4 is a flow chart, showing a method for measuring a permittivity of one embodiment of the present invention.

Referring to FIG. 1 and FIG. 4, a method for measuring a permittivity of the present invention is described. First, a resonant chamber 11 is provided (S41). The structure of the resonant chamber 11 is the same as the above-mentioned, and is thus omitted herein. Then, a sample 20 is disposed on the platform 13 within the resonant chamber 11 (S42), and a microwave MW is introduced into the cavity 111 of the resonant chamber 11 (S43). Then, a resonant frequency of the microwave MW is detected when resonance occurs within the cavity 111 (S44). Finally, a permittivity corresponding to the measured resonant frequency is calculated based on a corresponding relationship between resonant frequency and permittivity (S45). As the above-mentioned, the corresponding relationship between resonant frequency and permittivity can be obtained from a simulation performed by an electromagnetic field simulation software.

Figure 6:
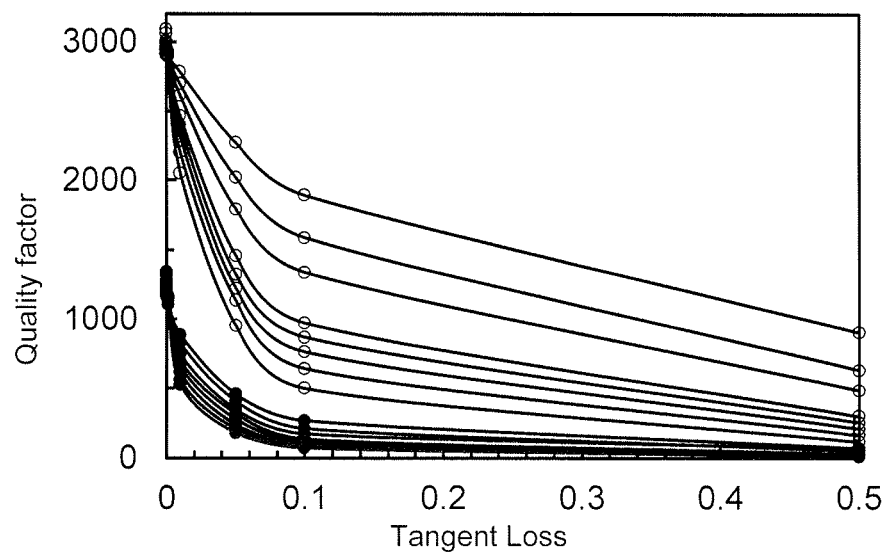
FIG. 6 is a curve diagram, showing a corresponding relationship between Quality factor and Tangent Loss.

FIG. 5 shows a corresponding relationship between resonant frequency and permittivity, which is obtained from a simulation performed by HFSS software. In FIG. 5, hollow circles represent a simulation performed by a conventional measuring system without a pillar disposed, and the Tangent Loss is from 0 to 0.1. Solid circles represent a simulation performed by a measuring system of the present invention with a pillar disposed, and the Tangent Loss is from 0 to 0.1. Hollow squares represent a simulation performed by a conventional measuring system without a pillar disposed, and the Tangent Loss is 0.5. Solid squares represent a simulation performed by a measuring system of the present invention with a pillar disposed, and the Tangent Loss is 0.5. FIG. 6 shows a relation diagram between different Tangent Loss and corresponding Quality factor (Q factor), simulated by the HFSS software. In FIG. 6, the hollow circles from bottom to top respectively represent simulation results performed by a conventional measuring system without a pillar disposed when a set permittivity is 2, 4, 6, 8, 10, 20, 30, 100; and the solid circles from bottom to top respectively represent simulation results performed by a measuring system of the present invention with a pillar disposed when a permittivity is 2, 4, 6, 8, 10, 100, 20, 30.

It is appreciated from the Quality factor in FIG. 6, different Tangent Loss will cause a much stronger signal in the measuring system of the present invention with a pillar disposed than that in the conventional measuring system without a pillar disposed. When the Tangent Loss is too small, a signal of the conventional measuring system will be dramatically disturbed by the unexpected resonance system. Therefore, the conventional measuring system may only be suitable for a range of larger Tangent Loss. In contrast, the expected signal of the measuring system of the present invention may be enhanced, and therefore, measurements can be done for the Tangent Loss from 0 to larger range. Besides, it is appreciated from FIG. 5, in the conventional measuring system, the resonant frequency variation corresponding to different permittivity may be smaller, so that it is difficult to be measured, and small perturbations generated by unexpected factors will seriously impact the accuracy of the measurement. In contrast, in the measuring system of the present invention, the resonant frequency variation corresponding to different permittivity may be larger, so that small perturbations generated by unexpected factors may be neglected, and the accuracy of the measurement is enhanced. Moreover, the measuring system of the present invention may be used for measuring permittivity in a much broader range in comparison to the conventional measuring system.

The measuring system of the present invention is verified below with different samples. The HFSS simulation result where no sample is disposed within the measuring system shows that a simulated resonant frequency is 3.1601 GHz and the Quality factor is 1490. The actual measurement show that a measured resonant frequency is 3.16075 GHz and the Quality factor is 1580. Table 1 is the HFSS simulation results and measurement results of Teflon, wherein a height of the platform is 14.85 mm, the permittivity is 2.08, and the Tangent Loss is about 0.0002.

TABLE 1

|  | Resonant frequency (GHz) | Quality factor | Volume of the sample (mm³) |
|---|---|---|---|
| HFSS | 2.33730 | 817.0 | 999.28 |
| 1 | 2.34725 | 1043.2 | 1000.04 |
| 2 | 2.34750 | 1043.3 | 1004.05 |
| 3 | 2.34775 | 1074.5 | 998.79 |
| 4 | 2.34750 | 1104.7 | 1000.79 |
| 5 | 2.34763 | 1043.4 | 998.03 |
| 6 | 2.34825 | 1043.7 | 1000.04 |
| 7 | 2.34725 | 1043.2 | 998.79 |
| 8 | 2.34750 | 1043.3 | 1000.79 |
| 9 | 2.34800 | 1104.9 | 996.78 |
| 10 | 2.349125 | 1105.5 | 996.78 |
| average | 2.35 | 1064.98 | 999.49 |
| error | 0.45% | 30.35% | 0.02% |
| standard deviation | 0.000568 | 29.27 | 2.18 |

Table 2 is the HFSS simulation results and measurement results of Quartz, wherein a height of the platform is 14.85 mm, the permittivity is 3.78, and the Tangent Loss is about 0.

TABLE 2

|  | Resonant frequency (GHz) | Quality factor | Volume of the sample (mm³) |
|---|---|---|---|
| HFSS | 2.259200 | 728.0 | 999.28 |
| 1 | 2.259000 | 1004.0 | 1021.19 |
| 2 | 2.258000 | 1003.6 | 1018.65 |
| 3 | 2.259875 | 1063.5 | 1017.90 |
| 4 | 2.257625 | 1003.4 | 1017.37 |
| 5 | 2.259375 | 1063.2 | 1017.37 |
| 6 | 2.261000 | 1064.0 | 1014.62 |
| 7 | 2.259000 | 1063.1 | 1019.17 |
| 8 | 2.260375 | 1130.2 | 1015.36 |
| 9 | 2.257000 | 1062.1 | 1019.38 |
| 10 | 2.261000 | 1130.5 | 1015.36 |
| average | 2.259225 | 1058.75 | 1017.64 |
| error | 0.00% | 45.43% | 1.84% |
| standard deviation | 0.001382 | 46.50 | 2.07 |

Table 3 is the HFSS simulation results and measurement results of aluminum and Table 4 is the HFSS simulation results and measurement results of copper, wherein a height of the platform is 14.71 mm.

TABLE 3

|  | Resonant frequency (GHz) | Quality factor | Volume of the sample (mm³) |
|---|---|---|---|
| HFSS | 2.0816 | 703 | 1012.47 |
| measurement results | 2.0816 | 925 | 1012.47 |
| error | 0.00% | 31.60% | 0.00% |

TABLE 4

|  | Resonant frequency (GHz) | Quality factor | Volume of the sample (mm³) |
|---|---|---|---|
| HFSS | 2.079000 | 721 | 1025.00 |
| 1 | 2.083675 | 981 | 1025.02 |
| 2 | 2.069425 | 828 |  |
| 3 | 2.083550 | 936 |  |
| 4 | 2.074800 | 593 |  |
| average | 2.077863 | 834 | 1017.64 |
| error | 0.05% | 15.73% | 0.72% |
| standard deviation | 0.0069 | 173.38 |  |

Table 5 is the measurement results of Pallisandro, Obsidian, Green crystal, Yellow crystal, Pink crystal, and Ocher.

TABLE 5

| Samples | Pallisandro | Obsidian | Green crystal | Yellow crystal | Pink crystal | Ocher |
|---|---|---|---|---|---|---|
| radius (mm) | 10.4 | 10.25 | 10.275 | 10.4 | 10.54 | 10.05 |
| resonant frequency (GHz) | 2.42775 | 2.507 | 2.6055 | 2.3555 | 2.5695 | 2.62575 |
| Quality factor | 249 | 176 | 549 | 448 | 381 | 218 |
| permittivity | 7.34 | 6.122 | 4.707 | 8.941 | 4.762 | 4.65 |
| Tangent Loss | 0.0095 | 0.015 | 0.0001115 | 0.001087 | 0.001526 | 0.012 |

It is appreciated from the above verification results that the system for measuring a permittivity of the present invention may be capable of measuring permittivity in a broader range and achieve higher accuracy.

To sum up the foregoing descriptions, the system and method for measuring a permittivity of the present invention can enhance the electric field intensity around a sample, so that a perturbation of the resonant system is amplified by the sample. Therefore, small perturbations generated by unexpected factors are relatively smaller and will not impact the accuracy of the measured permittivity, so that the accuracy of the measurement may be enhanced greatly. Besides, the system and method for measuring a permittivity of the present invention may be capable of measuring permittivity in a broader range.

While the invention is susceptible to various modifications and alternative forms, a specific example thereof has been shown in the drawings and is herein described in detail. It should be understood, however, that the invention is not to be limited to the particular form disclosed, but to the contrary, the invention is to cover all modifications, equivalents, and alternatives falling within the spirit and scope of the appended claims.

What is claimed is:

1. A system for measuring a permittivity, comprising:
    a resonant chamber having a cavity;
    a conductive probe passing through a chamber wall of the resonant chamber and configured to introduce a microwave into the cavity of the resonant chamber;
    a platform disposed in the cavity of the resonant chamber and configured to carry a sample;
    a pillar disposed between the platform and the chamber wall so that the platform protrudes from the chamber wall to enhance an electric field intensity around the sample so as to amplify a perturbation of the resonant chamber by the sample;
    a detector configured to detect the resonant frequency of the microwave when resonance occurs within the cavity; and
    a computing module configured to calculate a permittivity corresponding to the resonant frequency of the sample within the cavity measured by the detector based on a corresponding relationship between resonant frequency and permittivity obtained from a simulation performed by an electromagnetic field simulation software.

2. The system for measuring a permittivity according to claim 1, wherein the platform and the pillar are cylindrical, and a diameter of the pillar is less than, equal to, or more than a diameter of the platform.

3. The system for measuring a permittivity according to claim 1, wherein the cavity is cylindrical.

4. The system for measuring a permittivity according to claim 1, wherein the conductive probe and the platform are correspondingly disposed.

5. The system for measuring a permittivity according to claim 1, wherein an included angle exists between an extending direction of the conductive probe and an extending direction of the pillar.

6. The system for measuring a permittivity according to claim 1, wherein an extending direction of the conductive probe and an extending direction of the pillar are perpendicular to each other.

7. The system for measuring a permittivity according to claim 1, wherein the conductive probe and the detector are integrated.

8. The system for measuring a permittivity according to claim 1, wherein a length of the conductive probe, which protrudes from the chamber wall, is adjustable.

9. The system for measuring a permittivity according to claim 1, wherein a height of the platform, which protrudes from the chamber wall, is adjustable.

10. The system for measuring a permittivity according to claim 1, wherein a carrying surface of the platform is a plane or comprises a trench or notch.

11. The system for measuring a permittivity according to claim 1, wherein the corresponding relationship between resonant frequency and permittivity is obtained from a simulation performed by an electromagnetic field simulation software.

12. A method for measuring a permittivity, comprising:
    providing a resonant chamber having a cavity and a platform, wherein the platform protrudes from a chamber wall of the resonant chamber with a pillar to enhance an electric field intensity around the sample so as to amplify a perturbation of the resonant chamber by the sample;
    disposing a sample on the platform;
    introducing a microwave into the cavity of the resonant chamber;
    detecting the resonant frequency of the microwave when resonance occurs within the cavity; and
    calculating a permittivity corresponding to the resonant frequency of the sample within the cavity based on a corresponding relationship between resonant frequency and permittivity obtained from a simulation performed by an electromagnetic field simulation software.

13. The method for measuring a permittivity according to claim 12, wherein the platform and the pillar are cylindrical, and a diameter of the pillar is less than, equal to, or more than a diameter of the platform.

14. The method for measuring a permittivity according to claim 12, wherein the cavity is cylindrical.

15. The method for measuring a permittivity according to claim 12, wherein a height of the platform, which protrudes from the chamber wall, is adjustable.

16. The method for measuring a permittivity according to claim 12, wherein a carrying surface of the platform is a plane or comprises a trench or notch.

17. The method for measuring a permittivity according to claim 12, wherein the corresponding relationship between resonant frequency and permittivity is obtained from a simulation performed by an electromagnetic field simulation software.

* * * * *